United States Patent [19]

Rotramel et al.

[11] Patent Number: 4,511,579

[45] Date of Patent: Apr. 16, 1985

[54] PEST REPELLANT

[75] Inventors: George L. Rotramel; Daniel P. Veilleux, both of Raleigh; Joseph L. Allen, Durham, all of N.C.

[73] Assignee: Union Carbide Corporation, Danbury, Conn.

[21] Appl. No.: 549,747

[22] Filed: Nov. 8, 1983

Related U.S. Application Data

[63] Continuation-in-part of Ser. No. 248,247, Mar. 27, 1981, abandoned.

[51] Int. Cl.$^3$ ............................................. A01N 47/10
[52] U.S. Cl. .................................................... 514/490
[58] Field of Search ........................................ 424/300

[56] References Cited

U.S. PATENT DOCUMENTS

| 3,130,122 | 4/1964 | Koderna et al. | 424/300 |
| 3,269,902 | 8/1966 | Goodhue et al. | 424/300 |
| 3,433,873 | 3/1969 | Reinert et al. | 424/263 |

OTHER PUBLICATIONS

Gustavson et al.—Applied Animal Ethology 8(1982), pp. 551–559, 9(1982/1983), pp. 379–387.
Slade et al.—Chemical Abstracts 73:34145y (1970).
Schafer et al.—J. Agr. Food Chem., vol. 15, No. 2, (1967), pp. 287–289.

Primary Examiner—Leonard Schenkman
Attorney, Agent, or Firm—Gerald L. Coon

[57] ABSTRACT

Substituted aryl alkylcarbamates have been found to provide outstanding pest repellancy when applied to desirable foliage or agronomic crops.

6 Claims, No Drawings

PEST REPELLANT

This application is a continuation-in-part of application Ser. No. 248,247, filed Mar. 27, 1981, now abandoned.

FIELD OF THE INVENTION

This invention relates generally to the use of substituted aryl carbamates and, more particularly, trialkylphenyl alkylcarbamates, wherein said alkyl groups have from 1 to 4 carbon atoms, in pest repellant compositions.

BACKGROUND OF THE INVENTION

Animal pests that attack foliage or crops are a common problem for both the individual homeowner and the large-scale farmer. By way of illustration, rabbits enjoy eating Spiraea bushes in the wintertime when snow covers other potential food. Blackbirds prefer eating ripe cherries from the framer's trees.

Such animals are particularly difficult to treat since they are desirable wildlife when not consuming agronomic crops or foliage. Proper treatment of such wildlife presumes that they be exposed only to relatively non-toxic substances, if possible.

Commercial products such as, for example, methiocarb have been developed to combat the above problems. It would be desirable, however, to develop a new bird and mammal repellent that is more effective than currently-available commercial pest-repellants and less hazardous to the repelled pest and non-target birds and other wildlife.

SUMMARY OF THE INVENTION

This invention relates to the use of trialkylphenyl alkycarbamates in the control of agronomic and horticultural pests. The invention encompasses the use of pest-repellant composition containing at least one of such compounds wherein said alkyl groups have from 1 to 4 carbon atoms.

The invention also encompasses the pest-repellant compositions themselves as well as concentrates thereof.

DESCRIPTION OF THE PREFERRED EMBODIMENTS

This invention relates to a process for reducing damage to agriculturally important products by bird or mammal pests, by inducing an aversion response to said products in said pests, which comprises contacting said pests while in their natural habitat with a bird or mammal aversion amount of at least one trialkylphenyl alkylcarbamate, wherein said alkyls have from 1-4 carbon atoms which has been applied to said products.

Compounds useful as active ingredients in the pest-repellant compositions of the present invention include all trialkylphenyl alkylcarbamates wherein said alkyl groups have from 1 to 4 carbon atoms. Preferred compounds within the scope of the present invention are 2,3,5-trimethylphenyl methylcarbamate and 3,4,5-trimethylphenyl methylcarbamate, alone or in weight ratio mixtures of 1:9 to 9:1 of the 2,3,5- to 3,4,5-isomers. These compounds can be used alone or in mixtures thereof, or they can be mixed with conventional pest-repellant compounds to form the active portion of new pest repellant compositions. The instant compounds are made in accordance with the known methods of U.S. Pat. No. 3,130,122, incorporated herein by reference.

The compounds useful as active ingredients in the instant invention are employed in an amount sufficient to produce an aversion response in the bird or other animal pest to be controlled with respect to the particular foliage or crop to be treated. This amount will vary over a wide range and the required amount to induce an aversion response will depend upon a variety of factors such as the nature of the pest, the nature of the crop or foliage, climatic conditions at the time of treatment, and the like. In general, however, preferred range of amounts of active carbamate in carrier would be from about 0.25 wt. percent to about 10 wt. percent, more preferably from about 0.5 percent to about 1.0 percent depending on the type of formulation, based on wt. % active plus carrier.

As used herein, the term "pest repellant" is intended to encompass pest-aversion responses induced in the target pest by any mode including, but not limited to, oral ingestion, inhalation, or by dermal application e.g., into the skin of the animal via application to the animal's perch, and the like.

Although not wishing to be bound by any particular theory, the compounds of the present invention are effective in producing an animal-pest aversion response after entering the bloodstream of the animal by conventional means.

Pest repellant compositions containing the above compounds as the active ingredient will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the active ingredient in water with the aid of suitable surface active emulsifying and dispersing agents.

The choice of dispersing and emulsifying agents and the amount employed is dictated by the nature of the composition and the ability of the agent to facilitate the dispersion of the active ingredient. Generally, it is desirable to use as little of the agent as is possible, consistent with the desired dispersion of the active ingredient in the spary so that rain does not re-emulsify the active ingredient after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carried such as clay, talc, bentonite, diatomaceous earth, fuller earth, and the like. In the formulation of the wettable powders the aforementioned dispersing agents as well as lignosulfonates can be included.

The required amount of the active ingredient contemplated herein may be applied per acre treated in from 1 to 3000 gallons or more of liquid carrier and/or diluent or in from about 5 to 7500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, baits, salves, lotions, suspensions, flowable liquids, emulsifiable concentrates, seed coatings, paints or granules for general use contain from about ¼ to about 15 pounds of active ingredient per acre.

When applied as seed treatments to protect crops from damage by birds and mammals, the instant compounds are preferably applied at rates ranging from 0.25 pounds to 1.0 pounds active ingredient per 100 pounds of seed.

When applied to growing or mature crops to protect from damage by birds and mammals, the instant compounds are preferably applied at rates ranging from 0.5–2.0 pounds active ingredient per 100 gallons of spray.

When applied as baits or as topical treatments, the instant compounds are preferably applied at rates of 100 to 500 parts per million. Baits may contain the compound on the bait surface as with sunflower seeds for aversion of birds and rats or they may contain the compound in a manufactured edible solid or liquid substrate as a wax block containing grain or an oil or sugar-containing drink.

Typical modes of treatment with active ingredients envisioned by the present invention include (a) post-emergent treatment of crops or foliage, (b) pre-emergent treatment of seed or seed-parts (e.g., tubers or sprouts), (c) granular application to the soil to produce an aversion-response to the granule and (d) spray the harvested crops or incorporate into the packages for harvested crops to protect the crops from rodents, and the like via the aversion mechanism. Mode (c) above could be used prior to the later application to the soil and crops of relatively toxic pesticides such as carbofuran in order to pre-condition avoidance of the granules by birds or other wildlife.

Other uses envisioned by the instant invention include application to animals to protect them from injury by themselves or by others of the same species. For example, application of a suspension of active carbamate to the tails of pigs can protect them from being bitten by other pigs during shipment and reduce losses due to infected wounds. Similar applications would protect birds such as chickens and turkeys from "picking" and reduce needs for de-beaking or blinders. Addition of active carbamate to wound dressings would reduce chewing and licking of woulds by treated animals.

Application to mammals which have an oral component to pre-copulatory behavior can prevent mating. Pest rodents such as rats, mice and squirrels can be controlled by this method. For example, a box is rigged to apply a dust or supsension of active carbamate to the hair of rodents which enter it to obtain food. Males and females so treated would not be expected to mate as a consequence of an aversion which is learned through licking other treated animals during pre-copulatory behavior.

The following examples are intended to illustrate, but not limit, the present invention:

EXAMPLE I

In order to demonstrate the effectiveness of the instant pest-repellant compositions as compared to commercial pest-repellant compositions, cherries were counted out on individual, cherry trees and divided into three groups, each group containing 1500 cherries, identified as Group A, Group B and Group C. Group A was sprayed with a pest-control composition of the present invention wherein the active portion used a 1:6 wt. ratio mixture of 2,3,5-trimethylphenyl methylcarbamate and 3,4,5-trimethylphenyl methylcarbamate, wherein the active mixture was applied in an amount of three lbs. active per acre. Group B was sprayed with a comparison pest-control composition, namely a commercial product, methiocarb, in an amount of three lbs. active per acre. Group C, the control group, was not sprayed.

The results appear in Table I which follows:

TABLE I

|  | Number of Cherries on Day Specified | | | |
| --- | --- | --- | --- | --- |
|  | Day 1 | Day 5 | Day 12 | Day 19 |
| Group A | 1500 | 963 | 698 | 0 |
| Group B | 1500 | 900 | 0 | 0 |
| Group C | 1500 | 0 | 0 | 0 |

EXAMPLE II

In order to test the aversion response in wild red-winged blackbirds with respect to untreated sunflowers by vitue of exposure to treated fallen sunflower seeds, a 30.48 meter×15.24 meter field of Interstate Hybrid #897 sunflowers was enclosed with 1" hexagonal nylon mesh to provide 4 equal-sized enclosures 15.24M×7.62M×3.81M. Each enclosure contained 300 untreated flowers in 15 rows. Approximately 35 wild trapped red-winged blackbrids were introduced into each enclosure. Damage to flower heads was assessed at weekly intervals for 5 weeks. Damage consisted of the percent of seeds 2 cm concentric arc removed from each flower head.

Approximately 2 kg of sunflower seeds and nuts treated with a 1:6 wt. ratio mixture of 2,3,5- and 3,4,5-trimethylphenyl carbamate (0.5 gm/kg) were spread at the end of the first week and then weekly in two different enclosures. Untreated seeds and nuts were spread in the other 2 enclosures. Small piles of wheat screenlings and cracked corn were provided in each enclosure as an alternate food source.

The results indicated that percent of increase in head damage was decreased by 36.5% in the treated enclosures over the untreated check indicating that the birds learned to transfer their aversion from treated seeds on the groud to untreated seeds on the flower heads.

Comparable results were achieved using the same procedure and amounts of methiocarb. However, the instant carbamate mixture is much less toxic to birds than is methiocarb. For example, the $LD_{50}$ (lethal dosage) for starlings of the above mixture is greater than 100 mg/kg, whereas the $LD_{50}$ for methiocarb is only 12 mg/kg.

EXAMPLE III

Norway rats were divided into 3 groups. Group A was exposed to a choice between untreated unpreferred unsweetened cornmeal and preferred sweetened corn meal that had been treated with the carbamate mixture of Examples I and II at a level of 40 ppm.

Group B was allowed to eat untreated sweetened corn meal followed by injection of 18 mg/kg of the same carbamate mixture.

Group C (control group) was given the choice between untreated sweetened corn meal and untreated unsweetened corn meal.

The results indicated that Group A consumed 75% of the amount of preferred food that was eaten by Group C whereas Group B consumed only 2% of the preferred food eaten by Group C.

What is claimed is:

1. A process for reducing damage to agriculturally important products by bird or mammal pests, by including an aversion response to said products in said pests, which comprises contacting said pests while in their natural habitat with a bird or mammal aversion amount of at least one trialkylphenyl alkylcarbamate, wherein said alkyls have from 1–4 carbon atoms which has been applied to said products.

2. A process in accordance with claim 1 wherein said contacting is accomplished via ingestion of said trialkylphenyl alkylcarbamate by said pests.

3. A process in accordance with claim 1 wherein said contacting is accomplished via inhalation of said trialkylphenyl alkylcarbamate by said pests.

4. A process in accordance with claim 1 wherein said contacting is accomplished as a result of the treatment of said agriculturally important product with trialkylphenyl alkylcarbamate.

5. A process in accordance with claim 1 wherein said trialkylphenyl alkylcarbamate is a trimethylphenyl methylcarbamate.

6. A process for inducing an aversion-response by animal pests to toxic pesticide granules which comprises, prior to treating soil with said toxic granules, applying to said soil placebo granules containing an aversion-effective amount of at least one trialkyl-phenyl alkylcarbamate, wherein said alkyls have from 1 to 4 carbons.

* * * * *